(12) United States Patent
Janin et al.

(10) Patent No.: US 7,970,202 B2
(45) Date of Patent: Jun. 28, 2011

(54) METHOD AND ARRANGEMENT FOR DETECTING SURFACE AND STRUCTURAL DEFECTS OF A LONG MOVING PRODUCT

(75) Inventors: Pierre-Jean Janin, Les Essarts le Roi (FR); Mathieu Peyssard, Chatou (FR)

(73) Assignee: Siemens VAI Metals Technologies SAS, Saint-Chamond (FR)

( * ) Notice: Subject to any disclaimer, the term of this patent is extended or adjusted under 35 U.S.C. 154(b) by 741 days.

(21) Appl. No.: 11/922,075

(22) PCT Filed: Jun. 12, 2006

(86) PCT No.: PCT/FR2006/001322
§ 371 (c)(1),
(2), (4) Date: Apr. 17, 2008

(87) PCT Pub. No.: WO2006/134259
PCT Pub. Date: Dec. 21, 2006

(65) Prior Publication Data
US 2009/0245622 A1  Oct. 1, 2009

(30) Foreign Application Priority Data
Jun. 14, 2005  (FR) ...................................... 05 06039

(51) Int. Cl.
*G06K 9/00* (2006.01)
(52) U.S. Cl. ...................................................... 382/152
(58) Field of Classification Search .................. 382/141, 382/149, 152, 224; 348/86, 92, 125
See application file for complete search history.

(56) References Cited

U.S. PATENT DOCUMENTS

| | | | |
|---|---|---|---|
| 4,139,890 A | 2/1979 | Yerkes et al. | |
| 4,608,599 A | 8/1986 | Kaneko et al. | |
| 4,759,072 A | 7/1988 | Yamane et al. | |
| 5,654,977 A | 8/1997 | Morris | |
| 6,959,108 B1 * | 10/2005 | Bartelt et al. | 382/141 |

FOREIGN PATENT DOCUMENTS

| | | |
|---|---|---|
| EP | 0 105 401 | 4/1984 |
| EP | 0 974 833 | 1/2000 |
| JP | 04066225 | 3/1992 |
| WO | WO 01/17264 | 3/2001 |
| WO | WO 2004/051178 | 6/2004 |

OTHER PUBLICATIONS

Ceracki P. et al. "Online-Fehlererkennung Bei Warmband Durch Automatische Oberflaecheninspektion" Stahl Und Eisen, Verlag Stahleisen, Dusseldorf, DE, vol. 119, No. 4, Apr. 15, 1999, pp. 77-81, XP000830261.

* cited by examiner

*Primary Examiner* — Daniel G Mariam
(74) *Attorney, Agent, or Firm* — Laurence A. Greenberg; Werner H. Stemer; Ralph E. Locher (57) ABSTRACT

A method for detecting defects of a material moving in a rolling mill generally comprises illuminating product, obtaining (ACQ) image thereof in at least one spectral band, in pre-processing the formed image, in detecting and extracting (DTEXTR) eventually suspected areas of the pre-processed image, and in classifying (CLASS) the suspected areas into one or several defect or defect-free categories. For hot-rolled materials, the product is inspected in three disjointed spectral bands, including infrared, red and, for instance, green band in such a way that the suspected areas are classified into one or several defect-free or defect categories including the surface and structural defects.

7 Claims, 4 Drawing Sheets

METHOD AND ARRANGEMENT FOR DETECTING SURFACE AND STRUCTURAL DEFECTS OF A LONG MOVING PRODUCT

BACKGROUND (1) Field of the Invention

The present invention generally concerns techniques allowing the detection of any defects in a product moving in a rolling mill installation.

More precisely, the invention according to one first aspect concerns a defect detection method comprising at least one illuminating operation consisting of illuminating the moving product with a light source, an acquisition operation consisting of forming by scanning a first image of the moving product, as observed in a first spectral band of light, a pre-processing operation consisting at least of producing, from the first image of an observation area of the product, a first digitised luminosity distribution of this region, a detection and extraction operation of suspect zones consisting of using the first digitised luminosity distribution of the observation area of the product to detect the presence and location of any defects in this area, and a classification operation consisting at least of classifying suspect zones into one or more categories of defects or non-defects by comparison of the morphological and/or photometric characteristics of these suspect zones with morphological and/or photometric characteristics of known defects and of known non-defects, held in a pre-established database.

The digitised luminosity distribution is formed of pixels encoded over several bits and forms a normalized grey scale image corresponding to the distribution of luminosity of the image resulting from the acquisition, after correction of known distortions inherent in lighting and image taking.

(2) Prior Art

A method of this type is known to persons skilled in the art for cold rolled steel products, this method being particularly described in an article by Mr. Dominique Blanchard entitled "Automatic surface inspection system: experience and perspectives within the Usinor Group" published in June 2002 in "Revue de la Métallurgie" (Journal of Metallurgy).

This known method is of major interest for real-time inspection of cold-rolled steel products called "flats" i.e. products having a very high width/thickness ratio, typically greater than 100 or over.

Having regard to the very narrow thickness of these products, any defects which may affect them are likely to cause practically always deteriorations of their outer surface.

The situation is very different for products known as "long products" in steel-making, which are characterized by a section of geometric shape whose two main dimensions have a size of much the same magnitude, and which can be affected not only by surface defects but also by inner defects that are not revealed on the surface.

Long products are generally obtained from bulk billets that are continuously cast and then hot rolled in a succession of rolling mill stands arranged horizontally and vertically, these directions, for each mill stand, defining the orientation of the rotation axis of its working rolls. Rolling is conducted at high temperature, generally at around 1000° C. for steel, the invention not being limited however to steel and possibly being applied to other metals, in particular non-ferrous metals such as copper, or even to other materials.

The rolling of steel allows the size of the product to be reduced in two perpendicular directions while lengthening the product along the axis of the third direction. With this method it is possible to obtain special mechanical properties with a certain axial symmetry. Depending on the geometric shape of the section to be obtained, a greater or less number of mill stands are provided, and special section shapes can be achieved by using fluted rolls. The succession of section shapes of the product during lengthening, called roll pass design, plays a particularly important role to obtain the mechanical characteristics of the product in all the directions of this section. It is therefore possible to obtain products in bar form which may have a round or oval section, or even square, rectangular, hexagonal or octagonal. However, more complex, non-symmetric section shapes can also be achieved such as angle bars, I- or H-beams or rails.

Nonetheless said method had its disadvantages for the structure of the product, metal products in particular and especially in steel.

Defects of different origins may effectively come to be associated within the structure of the product, in particular surface defects due to mill scale which continues to adhere to the product surface and is caused by oxidation of the surface caused by water cooling of the mill stands. Since rolling is performed in two perpendicular directions in the horizontal stands and in the vertical stands, the scale may also penetrate inside the product with much more ease than in flat sheets whose thickness is always reduced in the same direction and is substantially reduced with respect to their width. Additionally, the use of fluted rolls for some mill stands may cause metal folds, which can cause some quantities of metal of different temperature to enter inside the product section thereby giving rise to heterogeneities. Finally, more upstream difficulties, such as poor lubrication when casting the billet or heat shock at the time of cooling, may generate structural defects of the metal which may come to be located inside the section of the product as well as on its surface after rolling.

It is therefore important, in particular for long products, to be able to detect not only surface defects but also defects present under the surface.

A technique to detect inner defects of a product is already known, based on analysis of the propagation of ultrasound waves inside this product. This technique, known as the Lamb wave technique, gives satisfactory results for the detection of inclusions, but requires the transmitter-sensor assembly to be in contact with the product to be inspected via an oil-water liquid layer to ensure proper transmission of the ultrasound waves. This constraint evidently means that the technique under consideration cannot be applied when the product to be inspected consists of a mass of steel at high temperature.

SUMMARY OF THE INVENTION

Within this context, the main object of the present invention is to enable the detection of any defects present under the surface of a product moving in a rolling mill, but ideally also to allow the detection of any surface defects of this product, in particular for long products.

For this purpose, the method of the invention, conforming to the general definition given in the above preamble, and intended to be applied to a product moving in a hot rolling installation and spontaneously emitting light radiation in a spontaneous emission spectrum including the infrared, is essentially characterized in that the illuminating operation is implemented by illuminating the moving product by a visible light source emitting at least outside the spontaneous emission spectrum, in that the acquisition operation consists of forming at least three images of the same observation area of this product in three respective non-contiguous spectral bands of which the first lies at least in the infrared, the second at least in the red and the third at least in part of the visible spectrum outside the spontaneous emission spectrum, in that the preprocessing operation is at least implemented on these three images to provide three respective luminosity distributions digitised over several bits, in that the detection and extraction operation of suspect zones is at least implemented on the three digitised luminosity distributions, and in that the classification operation consists of classifying at least the suspect zones extracted from the three digitised distributions into one or more categories of inner defects of the product, surface defects of the product or non-defects of the product at least by comparison of the morphological and/or photometric characteristics of these suspect zones and their scattering among the three digitised distributions with morphological and/or photometric characteristics and scattering among three corresponding digitised distributions of known inner defects, known surface defects and known non-defects, held in a pre-established database.

In other words, the method of the invention consists of analysing the images formed from the light emitted in the infrared band by the product itself and in particular by the inner part of its section, and images formed by light emitted by the surface, resulting either from the own emission of the product in the infrared range and in the visible range, or from reflection by the product of light provided by additional lighting. At the time of rolling, for example rolling steel conducted in the region of 1000° C., an important temperature gradient is formed between the centre of the section of the product and the surface, hence a light wavelength gradient of which only the part contained in the infrared range reaches the outside. On the other hand, the surface of the product emits light in the infrared range and in the visible range, particularly the red range.

Although the operation which consists of forming images of one same observation area of the product in different spectral bands is already described in U.S. Pat. No. 4,759,072 within the same context of a hot-rolled product, this prior art document does not at all raise the problem which consists of detecting the inner defects of this product, and therefore does not describe any means able to solve this problem.

According to the invention, provision is preferably made for the images to be formed using respective sensors at least sensitive to the infrared and producing respective raw images, for the first image to be formed in the infrared and obtained directly by capture of the first raw image behind an optical filter opaque to the radiations of wavelengths lower than the infrared, and for the second and third images to be respectively obtained from second and third raw images by subtraction of the first raw image.

The illuminating operation may consist of illuminating the product with a green light source, the third image then being formed in the green.

The pre-processing operation advantageously includes the production of a fourth digitised luminosity distribution, obtained by linear combination of the three original digitised distributions, this fourth distribution being used, for the detection and extraction operation and for the classification operation, in the same manner as the three original digitised distributions.

The method of the invention is particularly advantageous when the product moving on the hot-rolling installation is a long product i.e. a product whose cross-section is typically contained in a polygon, a circle or an ellipse, and at all events presents main dimensions having the same order of magnitude and which are much smaller than the length of the product, oriented in the moving direction of this product.

In this case, the observation area common to the three images extends over the entire perimeter of the product and over at least part of its length, and each of the three images may be formed by joining side by side at least two elementary images formed, in one same spectral band of light, over one same part of the length of the product and over complementary non-contiguous portions of the perimeter of this product.

The invention further concerns an installation for implementing a method such as previously described, this installation being characterized in that it comprises at least one digital camera CCD, provided with three linear detection arrays arranged transverse to the direction of travel of the product and sensitive to different colours of the spectrum of visible light.

The illuminating operation will be implemented using an auxiliary lighting device whose wavelength is advantageously chosen in a range distant from the red and infrared. In a particularly advantageous manner, these additional lighting means may consist of electroluminescent diodes (LEDs).

All the light radiation emitted or re-emitted by the product, if there are any product defects, will give images comprising different localized emission zones, and these defects may be detected, located and differentiated by analysis of the images formed from the different lights and by their comparison.

The acquisition of images is conducted continuously, the product being observed under a plurality of different angles relative to one same reference direction, said angles covering a sector of 360 degrees, so as to a form a continuous image of the entire perimeter of the product over a determined section of its length or the totality thereof. The acquisitions of all the images detected under the different angles are synchronized with each other so that it is possible, at a given time, to form a single image of the entire perimeter of the moving product at the same point of its length. Preferably, the acquisition of images is also synchronized with the travel of the product being rolled, so that it is possible to locate detected defects with respect to the length of the product.

An installation to detect defects of a moving long product during hot-rolling, according to the invention, comprises image formation, acquisition and processing means. These means are arranged in the spaces separating the vertical and horizontal mill stands of a hot-rolling installation for a product whose cross-section has a geometric shape that is little flattened e.g. circular, oval or polygonal whether regular or irregular. Preferably, the defect detecting equipment of an installation according to the invention is installed so that it can perform image acquisition of the moving product between the third and fourth mill stands of the hot-rolling mill.

The detection equipment and the additional lighting equipment are protected, according to the invention, against the atmosphere of the rolling mill and any possible damage by protection means and cooling means.

BRIEF DESCRIPTION OF THE DRAWINGS

Other characteristics and advantages of the invention will become more clearly apparent from the following description given by way of indication and in no way limiting, with reference to the appended drawings in which.

DETAILED DESCRIPTION OF THE PREFERRED EMBODIMENT(S)

Figure 1:
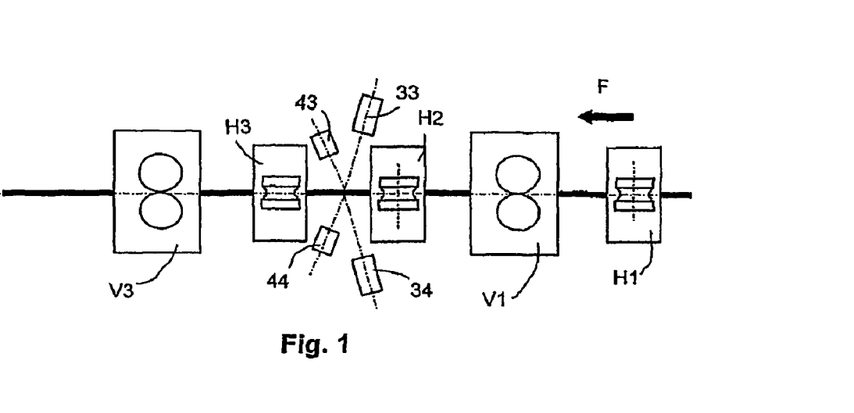
FIG. 1 is a schematic overhead view of part of a hot-rolling line for long products, equipped with a defect detection device according to the invention.
Figure 2:
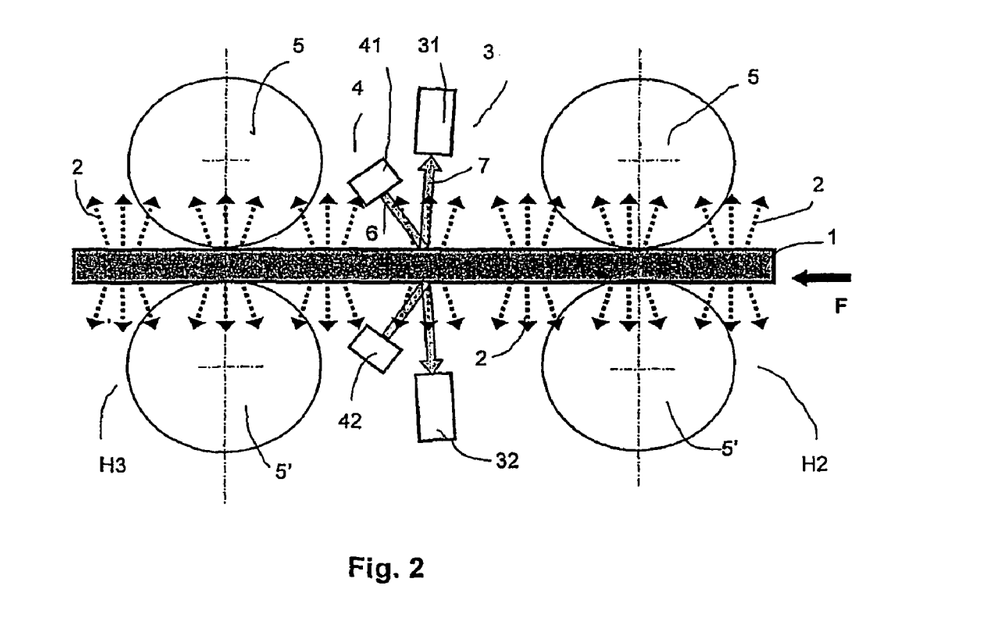
FIG. 2 is a schematic side view of the defect detection device according to the invention, installed in the rolling line.

As shown in FIGS. 1 and 2, a hot-rolling line for long products consists of a succession of horizontal and vertical mill stands. For example, the starting end of the rolling mill consists of mill stands H1, V1, H2, H3 and V2. The method of the invention allows the detection, using optical means, of the defects present on the surface and under the surface of the rolled product, irrespective of the shape of the section of the product. The light spontaneously emitted by the product is detected by a set of cameras arranged in housings 3 distributed all around the moving product in the direction indicated by arrow F. Preferably, this set of cameras 3 is installed between the third and fourth mill stands which are shown FIGS. 1 and 2 by horizontal mill stands H2 and H3. The light radiation 2 spontaneously emitted by the product lies in the visible spectrum and in the invisible spectrum, and propagates in all directions along the entire length of the product.

This spontaneous radiation is combined with the light supplied by additional lighting 4 and reflected by the surface of the product. This additional lighting is arranged in housings 4 installed all around the product, surrounding its travel axis. The light radiation 6 derived from this additional lighting housed in housings 4 is chosen in the range of visible wavelengths. This light radiation, after reflection on the surface of the product, can be captured by the cameras positioned in housings 3. In practice, it is therefore necessary to stagger housings 3 and housings 4 spatially so that the incident light illuminates the surface of the product at a certain angle and is generally reflected at another angle, i.e. the angle of vision of the cameras.

So as to be able to scan the entire surface of the product, a plurality of cameras is arranged at different angles relative to the horizontal and vertical planes passing through the travel axis of the product. Therefore FIG. 1 shows the housings 33 and 34 containing cameras, these housings being positioned in a horizontal plane passing through the travel axis of the product and being oriented, in this plane, at the same angle with respect to the travel axis, so that at a given time they can focus on the same section of the product.

A similar view is shown FIG. 2 which illustrates the housings 31 and 32 arranged in a vertical plane passing through the travel axis of the product and oriented in the same manner, so that the cameras they contain are able at a given time to focus on the same section of the moving product, which is also the section on which the cameras contained in housings 33 and 34 also focus on at the same time. Evidently, so that all the parts of the surface of the product 1 can be sufficiently and equivalently illuminated, each camera housing 31, 32, 33 and 34 is associated with a housing containing additional lighting 41, 42, 43 and 44. In the illustration shown FIGS. 1 and 2 there are therefore two housings 41, 42 positioned in the vertical plane passing through the travel axis of the product, and two lighting housings 43, 44 positioned in the horizontal plane passing through the travel axis. In each of these planes, the lighting is oriented relative to the axis of travel so that all the lighting housings project additional lighting on the same section of the moving product, this section being the one on which all the cameras contained in housings 31, 32, 33 and 34 also focus on at the same time.

Figure 3:
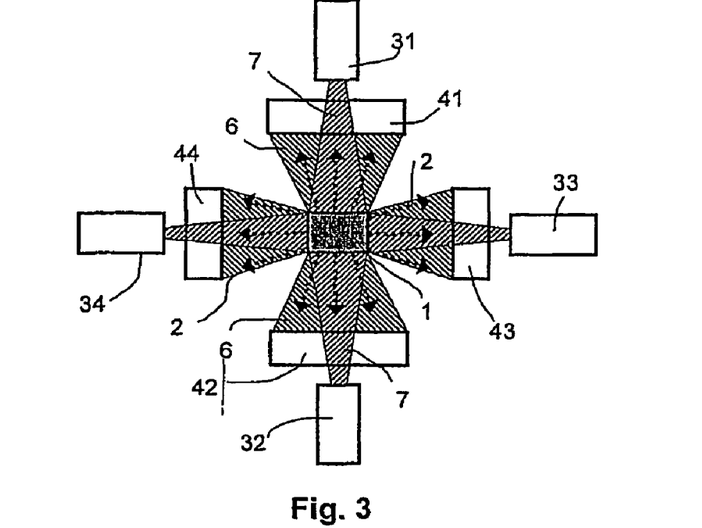
FIG. 3 is a schematic cross-sectional view of the defect detection device according to the invention for a rectangular product.
Figure 4:
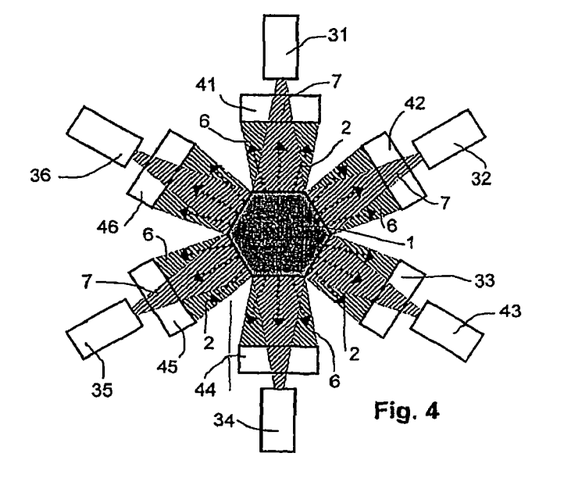
FIG. 4 is a schematic cross-sectional view of a defect detection device according to the invention for a hexagonal product.
Figure 5:
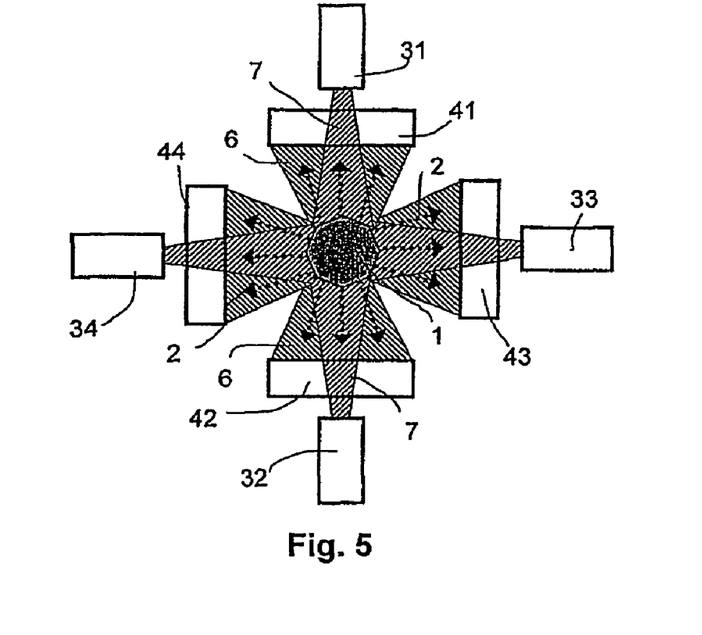
FIG. 5 is a schematic cross-sectional view of the defect detection device according to the invention for an octagonal product.

Said arrangement, comprising four lighting housings and four camera housings allows the inspection of any defects in a product of rectangular section, a cross-sectional view of this arrangement being shown FIG. 3. Depending on the shape of the section of the product 1, provision is made for a number of lighting devices 41, 42, . . . and camera housings 31, 32, 33, . . . so that images can be acquired of all the faces of the section of the moving product. For a product of octagonal section for example, it is possible to use the same arrangement as for a rectangular section, as shown FIG. 5. If the lighting devices 41, 42, 43 and 44 and camera housings 31, 32, 33 and 34 are oriented so that their axes pass through an axis of symmetry of the product section, each face of the product is oriented at an angle of 22.5° with respect to the axis of a lighting device or with respect to the axis of a camera housing. Therefore each of these devices is able to treat two adjacent faces of the section of the product at an angle of incidence that is fully acceptable for the quality of image to be formed, whether regarding the angle of incidence of the additional lighting or the focusing angle of the cameras. FIG. 4 shows an arrangement which can be used for a product having a hexagonal section. It is preferable in this case to provide for 6 sets of additional lighting 41, 42, 43, 44, 45 and 46, and 6 camera housings 31, 32, 33, 34, 35, 36. As shown FIG. 4, it is then easy to arrange the lighting and detection means so that the optical axes lie perpendicular to each of the faces of the product to be inspected.

More generally, if the section of the product 1 is more complex or irregular, a plurality of cameras is arranged all around the axis of travel over a complete angle sector of 360° so that the angles of vision cover the entirety of the perimeter of a section of product to be inspected.

The additional lighting means 41, 42, 43, . . . are chosen to provide a light 6 contrasting with the wavelengths lying in the red and infrared ranges, e.g. a yellow or blue light but advantageously a green light. These lighting means are preferably formed, in each housing, of a row of aligned electroluminescent diodes (LEDs). With these components, low cost lighting means can be achieved, the lamps having a long lifetime and not releasing any heat which is of importance since their implementation, their accessibility and their protection against the surrounding atmosphere require them to be enclosed in a housing. Powerful, costly cooling means are therefore avoided.

Each of the cameras advantageously consists of a colour camera generally equipped with three CCD arrays for linear detection, arranged transverse to the direction of travel of the product.

In front of these arrays are different, respective optical filters, each array during a given time interval thereby producing an elementary raw image of a portion of the perimeter of this product over a section of length corresponding to the distance traveled by this product during this time interval, this image being formed in a specific spectrum band corresponding to the chosen filter.

Therefore the array of sensitive CCD cells 313 of the camera 31 (FIG. 7) is preceded by a colour filter 311 which only allows infrared wavelengths to pass, the light from the product being concentrated on the arrays of each camera such as 31 by an optical device 312.

Figure 7:
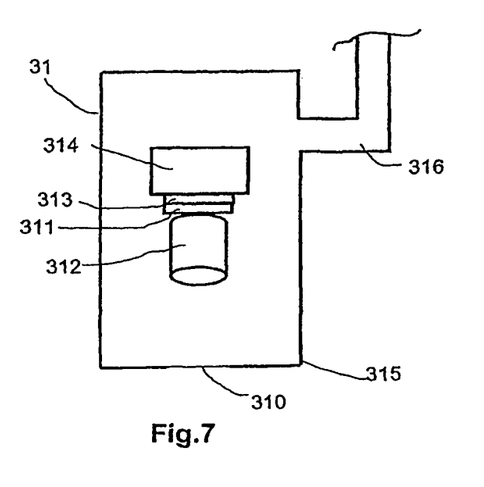
FIG. 7 is a diagram of the cameras of a defect detection device according to the invention, and their protection.

Similarly, a second array (not shown) of each camera such as 31 is preceded by a colour filter allowing the red light from the product to pass, and a third array (not shown) is preceded by a colour filter which for example allows the green light from the product to pass.

The first array of the camera 31, during a given time interval, therefore provides a first raw elementary image $I_{110}$, the second array of this camera 31 during this time interval providing a second raw elementary image $I_{210}$, and the third array of this same camera, during this same time interval, providing a third raw elementary image $I_{310}$.

The first index assigned to the images $I_{110}$, $I_{210}$, $I_{310}$, which assumes values 1, 2 and 3 respectively, is a reminder that these three raw elementary images are formed in three different, respective, spectral bands.

The second index assigned to the images $I_{110}$, $I_{210}$, $I_{310}$, which only assumes value 1, is a reminder that these three raw elementary images relate to one same first portion of the perimeter of the product.

And the third index assigned to the images $I_{110}$, $I_{210}$, $I_{310}$, which only assumes value 0, is a reminder that these three raw elementary images are those obtained before any processing.

Similarly, the different arrays of camera 32 will provide raw elementary images $I_{120}$, $I_{220}$, $I_{320}$, those of camera 33 will provide raw elementary images $I_{130}$, $I_{230}$, $I_{330}$, and those of camera 34 raw elementary images $I_{140}$, $I_{240}$, $I_{340}$.

In reality, irrespective of the spectrum band to which an array has a priori allocation, this array remains sensitive to infrared radiation so that, from the raw elementary images, elementary images must be formed that are corrected for this effect.

Since this remark obviously does not apply to the arrays arranged to produce an infrared elementary image, the elementary images $I_{110}$ $I_{120}$, $I_{130}$, and $I_{140}$, produced by the first arrays of cameras 31 to 34, directly form elementary images $I_{11}$, $I_{12}$, $I_{13}$ and $I_{14}$ of the product in the infrared.

On the other hand, elementary images $I_{21}$, $I_{22}$, $I_{23}$ and $I_{24}$ of the product in the red are obtained by subtracting, from the raw elementary images of the product in the red, the respective elementary images of the product in the infrared, i.e.

$$I_{21}=I_{210}-I_{11}; I_{22}=I_{220}-I_{12}; I_{23}=I_{230}-I_{13}; I_{24}=I_{240}-I_{14}$$

Similarly, the elementary images $I_{31}$, $I_{32}$, $I_{33}$ and $I_{34}$ of the product in the green are obtained by subtracting, from the raw elementary images of the product in the green, the respective elementary images of the product in the infrared, i.e.

$$I_{31}=I_{310}-I_{11}; I_{32}=I_{320}-I_{12}; I_{33}=I_{330}-I_{13}; I_{34}=I_{340}-I_{14}$$

Therefore, the elementary images produced by each portion of the perimeter of the product, e.g. elementary images $I_{11}$, $I_{12}$ and $I_{13}$, are formed in non-contiguous spectral bands, so that each elementary image formed in the green only contains information resulting from reflection of the green light by the surface of the product.

The method of the invention, for each camera and for example as camera 31, can use a CCD camera provided with standard red, green and blue image taking channels, placing in front of the blue channel array an optical filter opaque to radiation of wavelengths lower than the infrared, the resulting modified blue channel of the camera 31 supplying signal $I_{11}$.

A power and interface circuit 314 allows each camera to be connected to the electronic circuits for image acquisition 81, 82, 83, . . . . These circuits are installed in housings 31, 32, 33, . . . so that they can be installed in the hot-rolling mill in the immediate vicinity of the product. Housings 31, 32, 33, . . . consist of a hardened metal casing 315, 325, 335, . . . that is fully enclosed. These sets of housings are sealed and cooled by blown air 316, 326, 336, . . . . A thin transparent area on the front face of each housing 310, 320, 330, . . . allows reception of the light emitted by reflection and natural diffusion.

Figure 6:
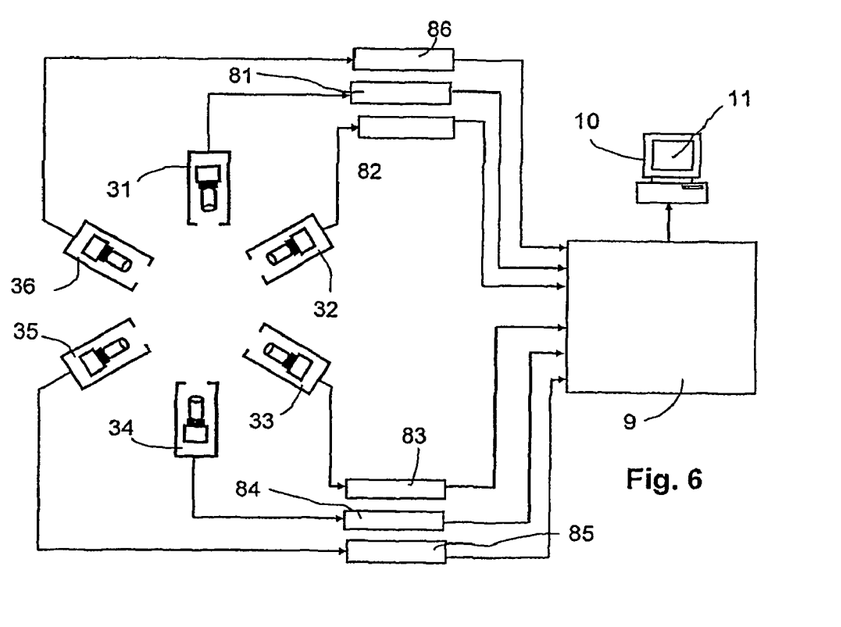
FIG. 6 is a simplified diagram of the image acquisition line according to the invention.

The elementary images acquired by the different cameras are synchronized with each other by the measurement line whose architecture is very schematically shown FIG. 6. The acquisitions are piloted by a calculator 9 which synchronizes all the acquisition electronic circuits 8 of the cameras. These acquisitions are made in real time and synchronized with the travel of the product 1 being rolled. The calculator 9 can therefore, at any time and on an operator's command and display device 10, reconstitute a complete image 11 of the perimeter of a section of the product, as seen at a given time. The elementary image acquired by each of the cameras for a certain time is juxtaposed with the image acquired by the neighbouring camera, thereby forming a complete continuous image of all the surface of the observed product 1. The synchronization of the acquisition of the images, as the product travels, allows the image thus formed to be located in relation to the length of the product.

It is therefore possible over one same time interval, i.e. on a determined section of length of the product, to obtain a complete image of the perimeter of this product in each of the three non-contiguous spectral bands, this complete image being obtained by placing side-by-side the elementary images formed in this band.

In other words, the joining side-by-side of elementary images $I_{11}$, $I_{12}$, $I_{13}$ and $I_{14}$ of the product in the infrared, derived from cameras 31 to 34 (FIG. 3 or 5), provides a complete image $I_1$ of the perimeter of this product in the infrared, the joining of elementary images $I_{21}$, $I_{22}$, $I_{23}$ and $I_{24}$ of the product in the red provides a complete image $I_2$ of the perimeter of this product in the red, and the joining of the elementary images $I_{31}$, $I_{32}$, $I_{33}$ and $I_{34}$ of this product in the green provides a complete image $I_3$ of the perimeter of this product in the green.

Figure 8:
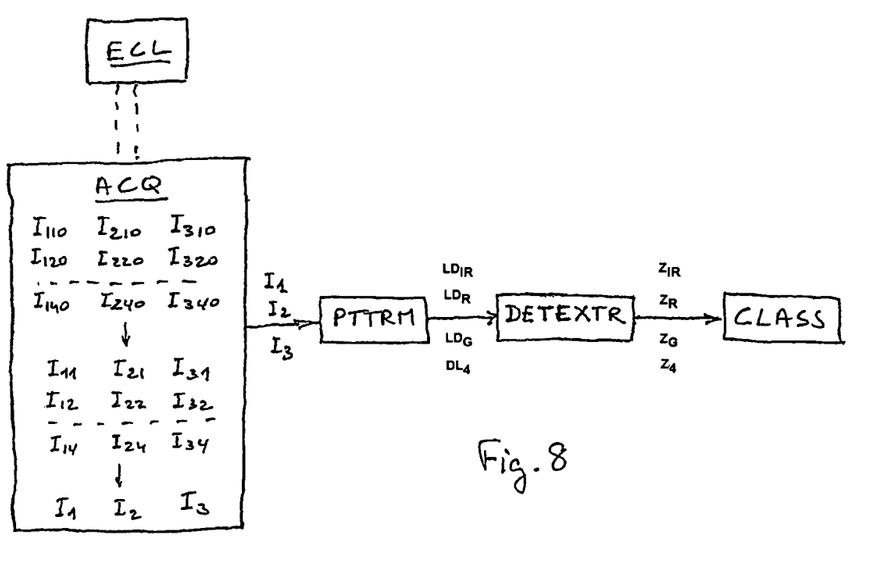
FIG. 8 is a diagram of the treatment applied by the calculator illustrated in FIG. 6 to the data it receives.

The complete images $I_1$, $I_2$, $I_3$ of the perimeter of the product, thus formed in the three spectral bands of the infrared, red and green, during acquisition ACQ (FIG. 8) concomitantly with lighting ECL of the product, consist of pixels coded over several bits and therefore form grey scale maps.

The calculator 9 also contains algorithms to process the images, enabling it to implement the method of the invention.

First, the calculator 9 must correct the complete images $I_1$, $I_2$, $I_3$ of the perimeter of the product, which suffer from various distortions resulting in particular from any defects in uniformity of lighting, vignetting of the lens 312 (FIG. 7) or variations in sensitivity between the cells of the different arrays of CCD sensors, and even between the arrays themselves.

To overcome these difficulties, the method of the invention implemented in the calculator 9 comprises a pre-processing operation PTTRM consisting of producing, from each of the images $I_1$, $I_2$, and $I_3$ of the same observation area of the product, a corresponding digitised luminosity distribution of this area, respectively $LD_{IR}$, $LD_R$, and $LD_G$.

The digitised distributions $LD_{IR}$, $LD_R$, and $LD_G$ consist of pixels encoded over several bits and therefore, like images $I_1$, $I_2$, and $I_3$, form grey scale maps of the perimeter of the product, respectively in the infrared, red and green, the digitised distributions $LD_{IR}$, $LD_R$, and $LD_G$ nonetheless differing from images $I_1$, $I_2$, and $I_3$ in that they are corrected, in manner known per se, for the previously mentioned distortions inherent in lighting and image taking.

Preferably, the pre-processing operation PTTRM also includes the production of an additional digitised distribution $LD_4$, obtained by linear combination of the three original digitised distributions $LD_{IR}$, $LD_R$, and $LD_G$.

The method of the invention also comprises a detection and extraction operation DETEXTR of suspect zones.

This operation consists of using each of the digitised distributions $LD_{IR}$, $LD_R$, $LD_G$ and $LD_4$ of the observation area of the product to detect the presence and location of any defects in this area.

This operation is implemented, in manner known per se, by applying to each digitised distribution a treatment of "contour detection" type (Prewitt, Sobel, gradient, etc.) or of grey level thresholding type. The resulting mapping, in each observation area of the product, identifies no more than two regions which may or may not be connected namely a region that is a priori normal and a region to be analysed. If a region to be analysed is identified, additional tests known per se are conducted on this so-called "binary" map to determine any suspect zones $Z_{IR}$, $Z_R$, $Z_G$ and $Z_4$ in the different distributions using morphological parameters (dimension, shape, orientation) and/or photometric parameters (grey scale statistics parameters).

Finally, the method of the invention comprises a classification operation CLASS consisting of classifying the suspect zones $Z_{IR}$, $Z_R$, $Z_G$ and $Z_4$ extracted from the digitised distributions $LD_{IR}$, $LD_R$, $L_{DG}$ and $LD_4$ in one or more categories of inner defects of the product, surface defects of the product or non-defects of the product.

Classification tools which may be used in the invention (Coulomb sphere, k closest possible neighbours, neurone networks, etc.) are already known and used in the prior art to classify suspect zones into surface defects of the product or into non-defects.

Classification is made using a previously established database of specifically analysed experiments, and by comparing morphological and/or photometric characteristics of the suspect zones appearing in two digitised distributions with the morphological and/or photometric characteristics via which known defects or known non-defects, archived in the pre-established database, appeared in two corresponding digitised distributions.

The invention extends the application of this technique and its classification tools, in particular to allow discrimination between surface defects and inner defects of the product.

To do so, the pre-established database is constructed so as to list the various appearances of various types of suspect zones which can definitely be likened to surface defects, to inner defects and to non-defects, these appearances consisting of morphological and/or photometric characteristics of these suspect zones and their scattering at least in the digitised distributions $LD_{IR}$, $LD_R$, $LD_G$ and preferably in distributions $LD_{IR}$, $LD_R$, $LD_G$ and $LD_4$.

The classification operation CLASS is then conducted by comparing the morphological and/or photometric characteristics of the suspect zones $Z_{IR}$, $Z_R$, $Z_G$ and $Z_4$ and their scattering in the digitised distributions $LD_{IR}$, $LD_R$, $LD_G$ and $DL_4$ with the morphological and/or photometric characteristics and scattering in the corresponding digitised distributions of known inner defects, known surface defects and known non-defects, held in the pre-established database.

Schematically, surface defects essentially show their presence in distributions $LD_G$ and $LD_4$, only marginally in distribution $LD_R$ but not in distribution $LD_{IR}$, whereas inner defects essentially show their presence in distributions $LD_{IR}$ and $LD_4$, only marginally in distribution $LD_R$ but not in distribution $LD_G$.

The reference signs inserted after the technical characteristics given in the claims are solely intended to facilitate comprehension of the claims and in no way limit their scope.

The invention claimed is:

1. A method for detecting defects of a product moving in a rolling mill, said method comprising the steps of illuminating the moving product at least once with a light source, forming by scanning a first image of the moving product as observed in a first spectrum band of light, producing from a first image of an observation area of the product a first digitized luminosity distribution of said area, using the first digitized luminosity distribution of the observation area of the product to detect the presence and location of any defects in said area, classifying suspect zones into at least one category of defects or non-defects by comparing morphological and/or photometric characteristics of said suspect zones with morphological and/or photometric characteristics of known defects and of known non-defects held in a pre-established database, applying said method to a product moving in a hot-rolling installation and spontaneously emitting a light radiation in a spontaneous emission spectrum including the infrared, said illuminating step being implemented by illuminating the moving product with a visible light source emitting at least outside the spontaneous emission spectrum, said scanning forming step comprising forming at least three images of the same observation area of said product in three respective non-contiguous spectral bands of which a first band lies at least in the infrared, a second band at least in the red, and a third band at least in part of the visible spectrum outside the spontaneous emission spectrum, said producing step being at least implemented on said three images to provide at least three respective luminosity distributions digitized over several bits performing a detection and extraction operation of suspect zones on the digitized luminosity distributions and said classifying step comprising classifying at least the suspect zones extracted from the digitized distributions into at least one category of inner defects of the product, surface defects of the product, and non-defects of the product at least by comparison of the morphological and/or photometric characteristics of said suspect zones and scattering of said suspect zones among the digitized distributions with the morphological and/or photometric characteristics and scattering among corresponding digitized distributions of known inner defects, known surface defects and known non-defects held in said pre-established database.

2. The method according to claim 1, comprising forming the images by means of respective sensors at least sensitive to the infrared and producing respective raw images forming the first image in the infrared and directly obtaining the first image by capture of the first raw image behind an optical filter opaque to radiations of wavelengths lower than the infrared, and obtaining the second and third images from the second and third raw images by subtracting the first raw image.

3. The method according to claim 1, wherein the illuminating step comprises illuminating the product with a green light source, and said forming step comprises forming said third image in the green.

4. The method according to claim 1, further comprising producing a fourth digitised luminosity distribution obtained by linear combination of the three original digitised distributions and using said fourth distribution for detection and extraction of said suspect zones and classifying said suspect zones.

5. The method according to claim 1, further comprising providing the product moving in the hot-rolling installation in the form of a long product, whose cross-section is contained in at least one of a polygon, a circle or an ellipse.

6. The method according to claim 5, comprising forming the observation area common to the three images so that said observation area extends over an entire perimeter of the product and over at least part of a length of the product, and forming each of the three images by joining side by side at least two elementary images formed in one spectral band of light over one part of the length of the product and over non-contiguous, complementary portions of the perimeter of said product.

7. An installation for implementing a method according to claim 1, said installation comprising at least one digital camera CCD provided with three linear detection arrays arranged transverse to a direction of travel of a moving product and sensitive to different colors of the spectrum of visible light.

* * * * *